United States Patent
Seong et al.

(10) Patent No.: US 9,619,879 B2
(45) Date of Patent: Apr. 11, 2017

(54) APPARATUS AND METHOD FOR DETECTING LESION AND LESION DIAGNOSIS APPARATUS

(75) Inventors: Yeong-Kyeong Seong, Suwon-si (KR); Moon-Ho Park, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 544 days.

(21) Appl. No.: 13/363,442

(22) Filed: Feb. 1, 2012

(65) Prior Publication Data
US 2013/0030278 A1   Jan. 31, 2013

(30) Foreign Application Priority Data
Jul. 25, 2011   (KR) .................. 10-2011-0073398

(51) Int. Cl.
*G06K 9/00*   (2006.01)
*G06T 7/00*   (2017.01)
*A61B 5/00*   (2006.01)

(52) U.S. Cl.
CPC .......... *G06T 7/0012* (2013.01); *A61B 5/0091* (2013.01); *G06T 2207/10072* (2013.01); *G06T 2207/10132* (2013.01); *G06T 2207/30068* (2013.01); *G06T 2207/30096* (2013.01)

(58) Field of Classification Search
USPC .......................................... 382/128; 82/128
See application file for complete search history.

(56) References Cited

U.S. PATENT DOCUMENTS

| | | | |
|---|---|---|---|
| 8,077,927 B1* | 12/2011 | Maltby, II | 382/113 |
| 8,218,852 B2* | 7/2012 | Cork et al. | 382/141 |
| 8,238,637 B2* | 8/2012 | Ratner et al. | 382/132 |
| 2004/0101181 A1* | 5/2004 | Giger et al. | 382/128 |
| 2006/0120608 A1* | 6/2006 | Luo | A61B 8/0825 382/224 |
| 2006/0247525 A1* | 11/2006 | Huo | G06T 7/0012 600/437 |
| 2007/0167749 A1 | 7/2007 | Yarnall et al. | |
| 2008/0089472 A1 | 4/2008 | Yoon | |
| 2008/0144941 A1* | 6/2008 | Togashi | G06K 9/4619 382/207 |
| 2010/0118124 A1 | 5/2010 | Kim et al. | |
| 2010/0158332 A1* | 6/2010 | Rico et al. | 382/128 |

FOREIGN PATENT DOCUMENTS

| | | |
|---|---|---|
| JP | 2009-225904 A | 10/2009 |
| KR | 10-2007-0104878 | 10/2007 |
| KR | 10-2008-0030745 | 4/2008 |
| KR | 10-2008-0041182 | 5/2008 |
| KR | 10-2008-0069307 A | 7/2008 |
| KR | 10-2010-0052405 | 5/2010 |
| KR | 10-2010-0071595 A | 6/2010 |
| WO | WO 2006/042163 A2 | 4/2006 |

\* cited by examiner

*Primary Examiner* — Hadi Akhavannik
(74) *Attorney, Agent, or Firm* — Jefferson IP Law, LLP

(57) ABSTRACT

An apparatus for detecting a lesion is provided. The apparatus includes an extracting unit configured to extract at least one tissue region from an image of tissue regions, a setting unit configured to set at least one of the at least one extracted tissue region as a lesion detection candidate region, and a detecting unit configured to detect a lesion from the lesion detection candidate region.

18 Claims, 16 Drawing Sheets

APPARATUS AND METHOD FOR DETECTING LESION AND LESION DIAGNOSIS APPARATUS

CROSS-REFERENCE TO RELATED APPLICATION

This application claims the benefit under 35 U.S.C. §119(a) of Korean Patent Application No. 10-2011-0073398, filed on Jul. 25, 2011, the entire disclosure of which is incorporated by reference for all purposes.

BACKGROUND

1. Field

The following description relates to an apparatus and a method for detecting lesions and a lesion diagnosis apparatus.

2. Description of the Related Art

With the advancement of surgery techniques, different kinds of minimum invasive surgeries have been developed. A minimum invasive surgery process represents a surgery method in which a medical operation may be performed by approaching a lesion using surgical instruments without incising skin and muscle tissues. The surgical instruments may include a syringe or a catheter. The medical operation may include a medicine injection, removal of lesions, appliance insertion etc. In order to perform the minimum invasive surgery process, doctors needs to locate the lesion. Also, in order to diagnose a disease, the doctors may need to determine the size, shape and location of the lesion.

Various medical imaging equipment have been developed that can aid in the detection of the size, shape and location of the lesion. These medical imaging equipment include a Computed Tomography (CT) system, a Magnetic Resonance Imaging (MRI) system, a Positron Emission Tomography (PET) system, a Single Photon Emission Computed Tomography (SPECT), etc.

However, it may be difficult to precisely extract a lesion since the images produced by theses medical imaging equipment are typically of poor quality. Accordingly, a need exists for a technology capable of precisely extracting a lesion.

SUMMARY

According to an aspect, an apparatus for detecting a lesion is provided. The apparatus includes an extracting unit configured to extract at least one tissue region from an image of tissue regions, a setting unit configured to set at least one of the at least one extracted tissue region as a lesion detection candidate region, and a detecting unit configured to detect a lesion from the lesion detection candidate region.

The extracting unit may extract the at least one tissue region from the image by comparing feature information of the image to feature information of the tissue regions.

The extracting unit may partition the image into a plurality of regions by performing an image segmentation on the image and compare feature information of the partitioned region with feature information of the tissue region to extracts the at least one tissue region from the image.

Each of the feature information of the image and the feature information of the tissue regions may be represented by brightness, color, texture, relative location and shape, or any combination thereof.

The image may correspond to an image of a breast, and the lesion detection candidate region corresponds to a mammary glandular tissue region.

The extracting unit may compare feature information of the image of the breast with feature information of the mammary glandular tissue region to extract the mammary glandular tissue region from the image of the breast.

The extracting unit may extract breast tissue regions from the image of the breast by partitioning the image of the breast into a plurality of regions by performing an image segmentation on the image of the breast and comparing feature information of the partitioned region with feature information of the tissue regions.

The extracting unit may extract a subcutaneous fat tissue region and a pectoralis muscle region and extract a region between the subcutaneous fat tissue region and the pectoralis muscle region as the mammary glandular tissue region.

Breast tissue regions of the image of the breast may include a subcutaneous fat tissue region, the mammary glandular tissue region and a pectoralis muscle region.

Feature information of the subcutaneous fat tissue region may indicate an upper location of the image, a darker brightness compared to other regions and a round shape, feature information of the pectoralis muscle region may indicate a lower location of the image and a band-like texture having a uniform direction, and feature information of the mammary glandular tissue region may indicate a location between subcutaneous fat tissue region and the pectoralis muscle region and a small spot like texture.

The extracting unit may perform a morphology operation to remove noise included in an image corresponding to the extracted tissue region.

The extracting unit may include a gabor filter, a spatial gray level dependence (SGLD) filter, or a wavelet filter.

The extracting unit may utilize a window having a size of N*N or N*M to extract feature information of the image.

In another aspect, a method for detecting a lesion is provided. The method includes extracting at least one tissue region from an image of tissue regions, setting at least one of the at least one extracted tissue region as a lesion detection candidate region, and detecting a lesion from the lesion detection candidate region.

The extracting of the at least one tissue region from the image may include comparing feature information of the image with feature information of the tissue regions.

The extracting of the at least one tissue region from the image may include performing an image segmentation on the image to partition the image into a plurality of regions, and comparing feature information of the partitioned region with feature information of the tissue regions.

The image may be an image of a breast, and the lesion detection candidate region may be a mammary glandular tissue region.

The extracting of the at least one tissue region from the image may include comparing feature information of the image of the breast with feature information of the mammary glandular tissue region to extract only the mammary glandular tissue region from the image of the breast.

The extracting of the at least one tissue region from the image includes extracting breast tissue regions from the image of the breast, the extracting breast tissue regions from the image of the breast may include performing an image segmentation on the image of the breast to partition the image of the breast into a plurality of regions, and comparing feature information of the partitioned region with feature information of the mammary glandular tissue region.

The extracting of the at least one tissue region from the image includes extracting a subcutaneous fat tissue region and a pectoralis muscle region from the image of the breast, and extracting a region between the subcutaneous fat tissue region and the pectoralis muscle region as the mammary glandular tissue region.

In another aspect, an apparatus for diagnosing a lesion is provided. The apparatus includes an image acquisition unit configured to photograph an inside of an organism to acquire an image, an lesion detecting unit including an extracting unit configured to extract at least one tissue region from the image, a setting unit configured to set at least one of the at least one extracted tissue region as a lesion detection candidate region and a detecting unit configured to detect a lesion from the lesion detection candidate region, and a lesion diagnosis unit configured to diagnose a name of disease based on the lesion detected by the lesion detecting unit.

The image may be an image of a breast, and the lesion detection candidate region is a mammary glandular tissue region.

In another aspect, a medical imaging device for detecting a lesion is provided. The device may include an extracting unit configured to set at least one tissue region, as a lesion detection candidate region, from an image of a plurality of tissue regions, and a detecting unit configured to detect a lesion from the lesion detection candidate region.

Other features and aspects may be apparent from the following detailed description, the drawings, and the claims.

Figure 1:
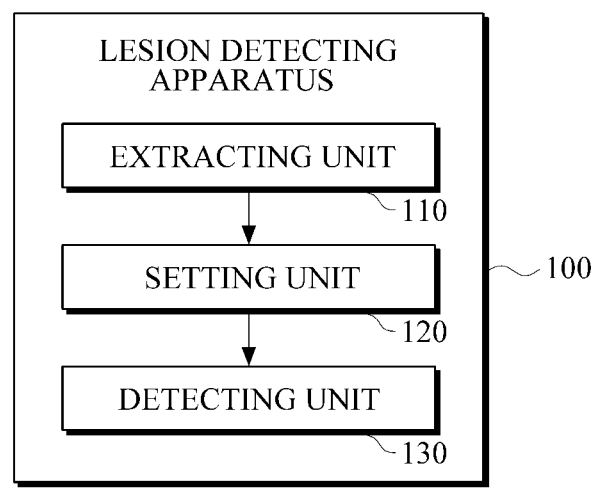
FIG. 1 is a diagram illustrating an example of a lesion detecting apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Hereafter, examples will be described with reference to accompanying drawings.

FIG. 1 illustrates an example of a lesion detecting apparatus.

Referring to FIG. 1, a lesion detecting apparatus 100 includes an extracting unit 110, a setting unit 120 and a detecting unit 130.

The extracting unit 110 may extract at least one tissue region from an image. The image may capture the inside of an organism and the image may include a plurality of tissue regions.

For example, the extracting unit 110 may use a window having a size of N*N or N*M to extract feature information of the image. The extracting unit 110 may compare feature information of the image with feature information of the tissue regions to extract the tissue region from the image. As an example, the extraction unit 110 may use a machine learning to extract the tissue region from the image. The machine learning may include a Support Vector Machine (SVM), a Random Forest (RF) classification, etc. The feature information of the image and the feature information of the tissue region may represent brightness, color, texture, relative location, shape, or any combination thereof. The extracting unit 110 may use a gabor filter, a spatial gray level dependence (SGLD) filter or a wavelet filter to extract texture feature information.

As another example, the extracting unit 110 may perform image segmentation on the image to partition the image into a plurality of regions. The extracting unit 110 may extract feature information for each partitioned region. The extracting unit 110 may compare the feature information of the partitioned region with feature information of the tissue region to determine the tissue region of the image.

Hereinafter, the description will be further made assuming that the image is an image of breasts and that a user or a manufacturer determines a mammary glandular tissue region as a lesion detection object region.

As another example, the extracting unit 110 may compare feature information of the image of the breasts with feature information of the mammary glandular tissue region. Subsequently, the extracting unit 110 may extract only the mammary glandular tissue region from the image of the breasts.

As yet another example, the extracting unit 110 may compare feature information of the image of the breast with feature information of the breast tissue region. Subsequently, the extracting unit 110 may extract a breast tissue region from the image of the breast. The breast tissue region includes a subcutaneous fat tissue region, the mammary glandular tissue region and a pectoralis muscle region. The subcutaneous fat tissue region may have a darker brightness than the brightness of other tissue regions and have a round shape. The pectoralis muscle region may have a band-like texture with a uniform direction. The mammary glandular tissue region may have a spot-like texture and exist between the subcutaneous fat tissue region and the pectoralis muscle region. As described above, the extracting unit 110 may extract only the mammary glandular tissue region or extract all of the breast tissue regions from the image of the breast.

As yet another example, the extracting unit 110 may perform an image segmentation on the image of the breast to partition the image of the breasts into a plurality of regions. The extracting unit 110 may extract feature information from each partitioned region. The extracting unit 110 may compare feature information of the partitioned region with feature information of the mammary grandular tissue region to extract a region. As described above, the extracting unit 110 may extract only the mammary glandular tissue region or extract all of the breast tissue regions from the image.

As yet another example, the extracting unit 110 may extract the subcutaneous fat tissue region and the pectoralis muscle region from the image of the breast. The extracting unit 110 may designate as the mammary glandular tissue region a region between the subcutaneous fat tissue region and the pectoralis muscle region.

The extracting unit 110 may perform a morphology operation to remove noise included in an image related to the extracted tissue region.

The setting unit 120 may set as a lesion detection candidate region at least one of the at least one extracted tissue region. For example, a user may specify a region having a higher chance of having a lesion than other regions as the lesion detection candidate region. As another example, in response to a user or a manufacturer specifying a cerebellum region and a muscle region as the lesion detection candidate region, the setting unit 120 may set the cerebellum region and the muscle region as the lesion detection candidate region. The cerebellum region and the muscle region may be regions among the extracted tissue regions. In response to the image being an image of a breast, a user or a manufacture may specify a mammary glandular tissue region as the lesion detection candidate region. The mammary glandular tissue region may be a region in which lesions more frequently occur than in other tissue regions. In this example, the setting unit 120 sets the mammary glandular tissue region among the extracted tissue regions as the lesion detection candidate region.

The detecting unit 130 may detect a lesion from the lesion detection candidate region. For example, the detection region 130 may detect information about the location, size and shape of the lesion. The detecting unit 130 may use an image segmentation scheme to detect a lesion. The image segmentation scheme may include a binary histogram thresholding method (BHT), a super-pixel scheme, or the like.

As described above, the lesion detecting apparatus may extract tissue regions from an image, set at least one of the extracted tissue regions as a lesion detection candidate region and perform detection only on the lesion detection candidate region. Accordingly, the chance of detecting a lesion may be increased and the time taken to detect a lesion may be reduced.

Figure 2:
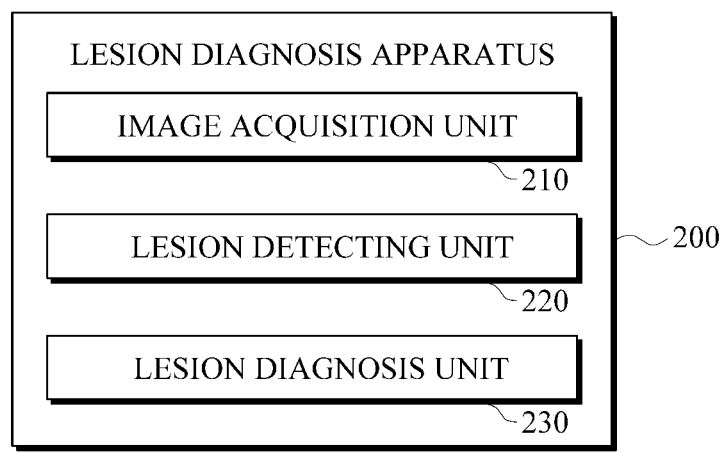
FIG. 2 is a diagram illustrating an example of a lesion diagnosis apparatus.

FIG. 2 illustrates an example of a lesion diagnosis apparatus.

Referring to FIG. 2, a lesion diagnosis apparatus 200 includes an image acquisition unit 210, a lesion detecting unit 220 and a lesion diagnosis unit 230.

The image acquisition unit 210 may capture the inside of an organism as an image. The image may include a plurality of tissue regions. For example, the image acquisition unit 210 may be a ultrasonic imaging system, a Computed Tomography (CT) system, a Magnetic Resonance Imaging (MRI) system, or any other system capable of photographing the inside of an organism.

The lesion detecting unit 220 may detect a lesion from the image generated by the image acquisition unit 210. For example, the lesion detecting unit 220 may extract information from the image about a lesion. The extracted information may include the location, size and shape of the lesion. The lesion detecting unit 220 may be implemented using a similar corresponding structure as that of the lesion detecting apparatus 100 shown in FIG. 1, and the lesion detecting unit 220 may have the same function as the lesion detecting apparatus 100. The lesion detecting unit 220 may include an extracting unit, a setting unit and a detecting unit. The extracting unit may extract at least one tissue regions from an image. The setting unit may set at least one of the extracted tissue regions as a lesion detection candidate region. The detecting unit may detect a lesion from the lesion detection candidate region. The extracting unit, the setting unit and the detecting unit may have substantially the same structures as the corresponding units shown in FIG. 1 and detailed descriptions thereof will be omitted for conciseness.

The lesion diagnosis unit 230 may diagnose the name of disease based on information from the lesion detected by the lesion detecting unit 220. For example, the lesion diagnosis unit 230 may diagnose the name of disease based on the information of the lesion, such as location, size and shape of the lesion.

As described above, the lesion diagnosis apparatus 200 may segment an image into a plurality of tissue regions, extract tissue regions from the image, set at least one of the extracted tissue regions as a lesion detection candidate region and perform detection only on the lesion detection candidate region. Accordingly, the lesion may be automatically detected and the name of disease may be diagnosed rapidly.

FIGS. 3A to 3D illustrate an example of a process of detecting a lesion by the lesion detecting apparatus of FIG. 1.

Hereinafter, a process of detecting a lesion from an image of the inner part of a breast produced by the lesion detecting apparatus will be described. However, the disclosure is not limited thereto, and the lesion detecting apparatus may detect lesions in other parts of a body in addition to the breast.

Figure 3A:
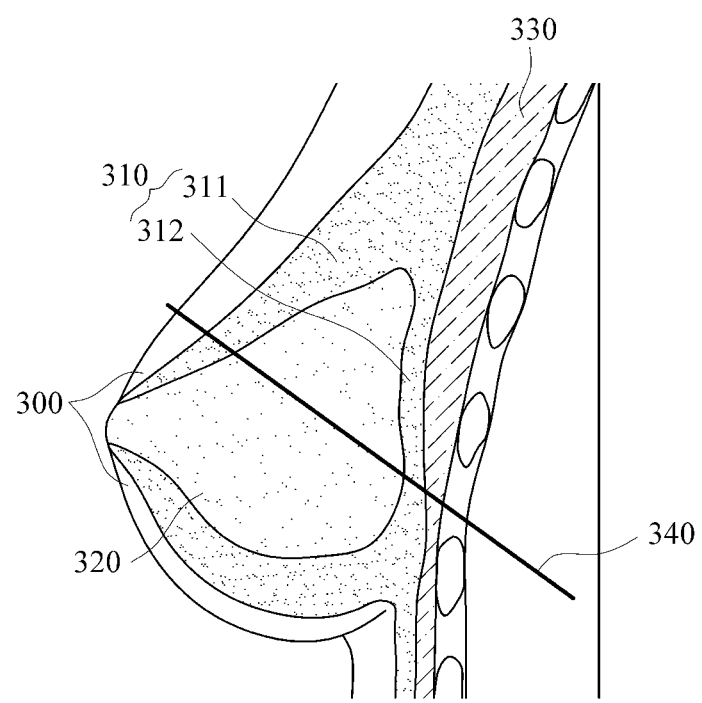
FIGS. 3A to 3D are diagrams illustrating an example of a process for detecting a lesion by the lesion detecting apparatus of FIG. 1.

FIG. 3A illustrates a side view of a breast.

Referring to FIGS. 1 and 3A, tissue regions of the breast include a skin region 300, a fat tissue region 310, a mammary glandular tissue region 320 and a pectoralis muscle region 330. The fat tissue region 310 includes a subcutaneous fat tissue region 311 and a retromammary fat region 312. Hereinafter, the following description is made on the assumption that an image of the breast is taken in the direction of leader line 340.

Figure 3B:
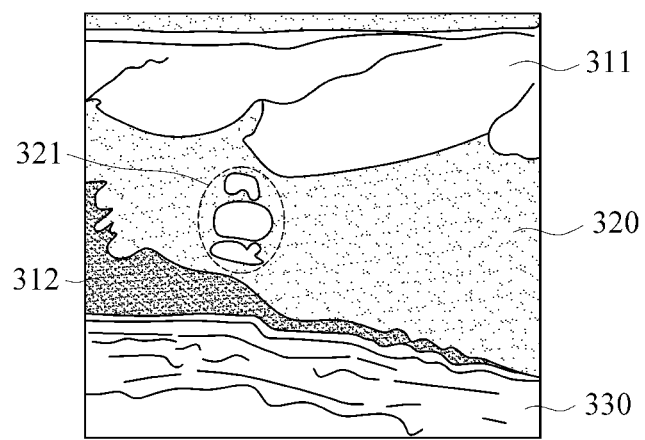

Referring to FIGS. 1 and 3B, tissue regions of the breast include the subcutaneous fat tissue region 311, the mammary glandular tissue region 320, the retromammary fat region 312 and the pectoralis muscle region 330. The mammary glandular tissue region 320 may include a lesion 321. The tissue regions of the breast may have feature information as follows. Feature information of the subcutaneous fat tissue region 311 and the retromammary fat tissue region 312 may indicate a darker brightness in comparison to other regions and a round shape. Feature information of the subcutaneous fat tissue region 311 may indicate an upper location of the image. Feature information of the mammary glandular tissue region 320 may indicate that the mammary glandular tissue region 320 is located at a location between the fat tissue region 310 and the pectoralis muscle region 330 and indicate a small spot like texture. Feature information of the pectoralis muscle region 330 may indicate a lower location of the image and indicate a band-like texture having a uniform direction.

Figure 3C:
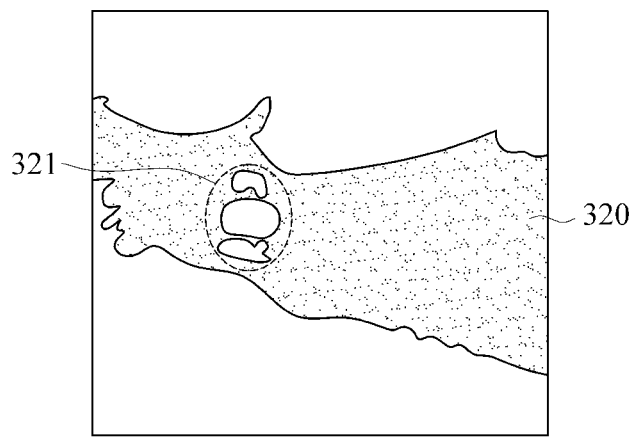

Referring to FIGS. 1 and 3C, the lesion detecting apparatus 100 may extract feature information of the image of the breast. For example, the lesion detecting apparatus 100 may use a window having a size of N*N or N*M to extract feature information of the image.

Hereinafter, the description will be made on the assumption that the mammary glandular tissue region 320 is set as the lesion detection candidate region.

For example, the lesion detecting apparatus 100 may compare feature information of the image of the breast with feature information of the tissue regions of the breast to extract tissue regions. The extracted tissue regions may include the subcutaneous fat tissue region 311, the retromammary fat region 312, the mammary glandular tissue region 320 and the pectoralis muscle region 330. The lesion detecting apparatus 100 may perform a morphology operation to reduce noise in an image corresponding to the extracted tissue region. The lesion detecting apparatus 100 may set the mammary glandular tissue region 320 as the lesion detection candidate region. The mammary glandular tissue region 320 may be one of the tissue regions among the extracted tissue regions 311, 312, 320 and 330.

For example, the lesion detecting apparatus 100 may compare feature information of the image of the breast with feature information of the mammary glandular tissue region 320 to extract the mammary glandular tissue region 320 from the image of the breast. Subsequently, the lesion detecting apparatus 100 may set the mammary glandular tissue region 320 as the lesion detection candidate region.

Figure 3D:
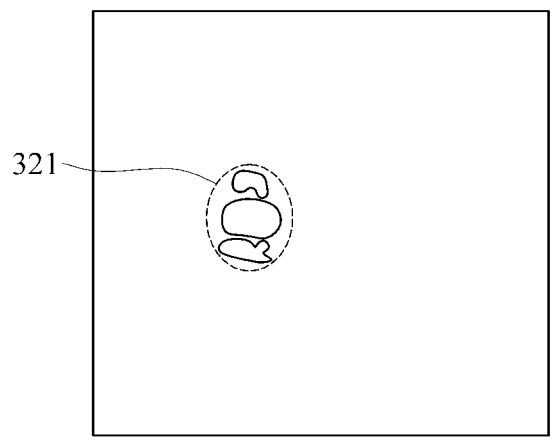

Referring to FIGS. 1 and 3D, the lesion detecting apparatus 100 may detect a lesion 321 from the lesion detection candidate region 320. For example, the lesion detecting apparatus 100 may use an image segmentation scheme to detect the lesion. The image segmentation scheme may include a binary histogram thresholding method (BHT), a super-pixel scheme, or the like.

As described above, the lesion detecting apparatus detects a lesion from the lesion detection candidate region having a higher chance of having lesions than other tissue regions. Accordingly, there is little need to perform lesion detection on the other tissue regions having a lower chance of having lesions. Accordingly, the time used to detect lesions is reduced and the lesions are more precisely detected.

FIGS. 4A to 4E illustrate another example of a process of detecting a lesion by the lesion detecting apparatus of FIG. 1.

Hereinafter, a process of detecting a lesion from an image of the inner part of a breast taken by the image acquisition unit will be described. However, the disclosure is not limited thereto, and the lesion detecting apparatus may detect lesions of other parts of a body in addition to the breast.

Figure 4A:
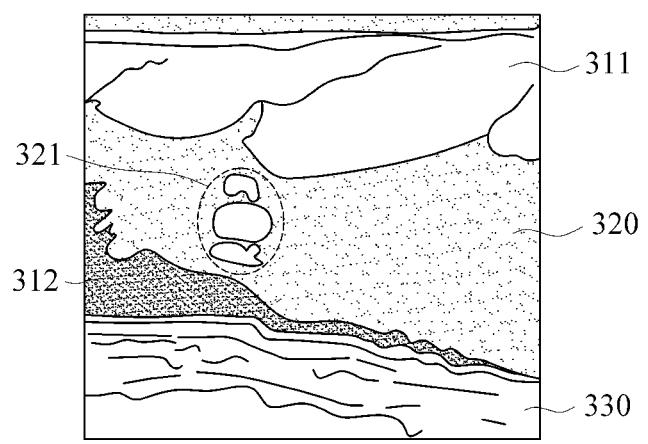
FIGS. 4A to 4E are diagrams illustrating another example of a process for detecting a lesion by the lesion detecting apparatus of FIG. 1.

Referring to FIGS. 1 and 4A, tissue regions of the breast include the subcutaneous fat tissue region 311, the mammary glandular tissue region 320, the retromammary fat region 312 and the pectoralis muscle region 330. The tissue regions of the breast may have feature information as follows. Feature information of the subcutaneous fat tissue region 311 and the retromammary fat tissue region 312 may indicate a darker brightness in comparison to other regions and a round shape. Feature information of the subcutaneous fat tissue region 311 may indicate an upper location of the image. Feature information of the mammary glandular tissue region 320 may indicate a location between the fat tissue region 310 and the pectoralis muscle region 330 and a small spot like texture. Feature information of the pectoralis muscle region 330 may indicate a lower location of the image and a band-like texture having a constant direction.

Figure 4B:
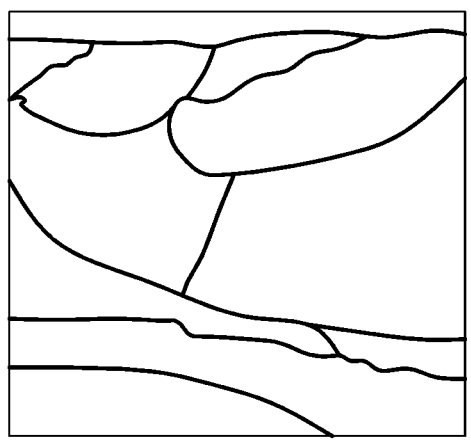

Referring to FIGS. 1 and 4B, the lesion detecting apparatus 100 may perform an image segmentation on the image of the breast to partition the image into a plurality of regions.

Figure 4C:
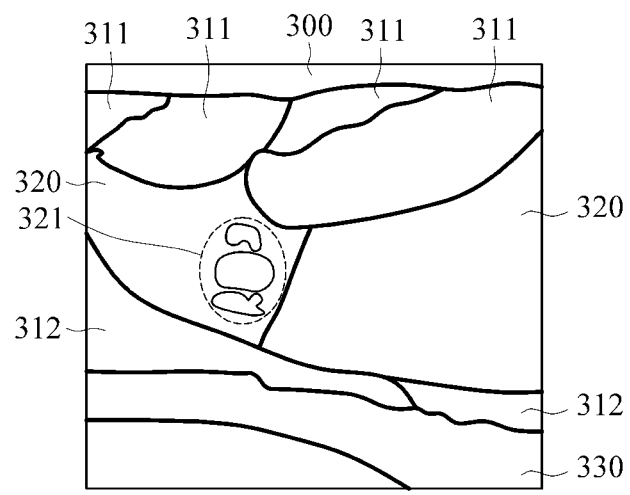

Referring to FIGS. 1 and 4C, the lesion detecting apparatus 100 may extract feature information from each partitioned region. The lesion detecting apparatus 100 may compare feature information of one partitioned region with feature information of one tissue region to recognize each of the partitioned regions corresponds to which tissue region. The lesion detecting apparatus 100 may extract the tissue regions 300, 311, 312, 320 and 330 from the image based on the recognized result.

Figure 4D:
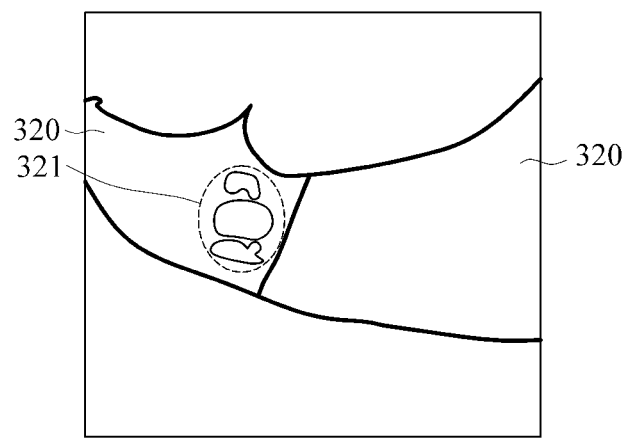

Referring to FIGS. 1 and 4D, the lesion detecting apparatus 100 may set the mammary glandular tissue region 320 as the lesion detection candidate region from among the tissue regions 300, 311, 312, 320 and 330.

Figure 4E:
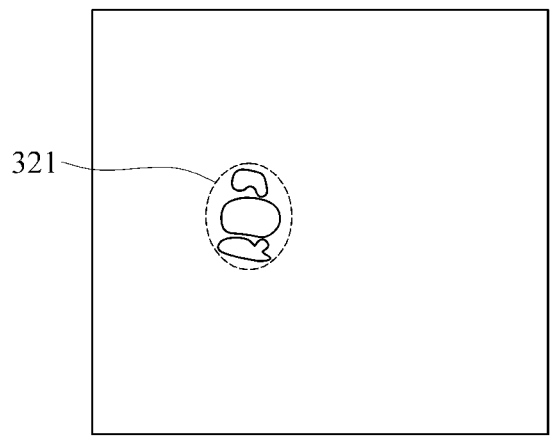

Referring to FIGS. 1 and 4E, the lesion detecting apparatus 100 may detect the lesion 321 from the lesion detection candidate region 320. For example, the lesion detecting apparatus 100 may use an image segmentation to detect the lesion. The image segmentation may include a binary histogram thresholding method (BHT), a super-pixel scheme, or the like.

As described above, the lesion detecting apparatus may partition the image of the breast into a plurality of regions and extract tissue regions of the image of the breast based on the feature information of each partitioned region, thereby improving the precision of extracting the tissue regions.

In addition, the lesion detecting apparatus may not need to perform lesion detection on tissue regions having a lower chance of having lesions, so that the time taken to detect lesions is reduced and the lesions are more precisely detected.

FIGS. 5A to 5D illustrate another example of a process of detecting a lesion by the lesion detecting apparatus of FIG. 1.

Hereinafter, a process of detecting a lesion from an image of the inner part of a breast taken by the image acquisition unit will be described. However, the disclosure is not limited thereto, and the lesion detecting apparatus may detect lesions of other parts of a body in addition to the breast.

Figure 5A:
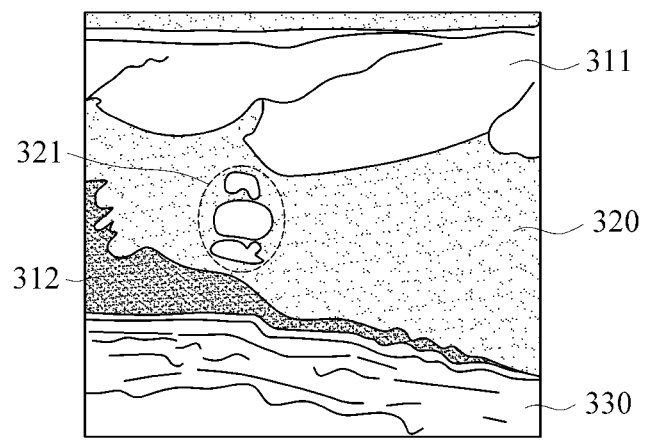
FIGS. 5A to 5D are diagrams illustrating yet another example of a process for detecting a lesion by the lesion detecting apparatus of FIG. 1.

Referring to FIGS. 1 and 5A, tissue regions of the breast include the subcutaneous fat tissue region 311, the mammary glandular tissue region 320, the retromammary fat region 312 and the pectoralis muscle region 330. The mammary glandular tissue region 320 may include a lesion 321. The tissue regions of the breast have feature information as follows. Feature information of the subcutaneous fat tissue region 311 and the retromammary fat tissue region 312 may indicate a darker brightness compared to other regions and a round shape. Feature information of the subcutaneous fat tissue region 311 may indicate an upper location of the image. Feature information of the mammary glandular tissue region 320 may indicate the location between the fat tissue region 310 and the pectoralis muscle region 330 and a small spot like texture. Feature information of the pectoralis muscle region 330 may indicate a lower location of the image and a band-like texture having a constant direction.

Figure 5B:
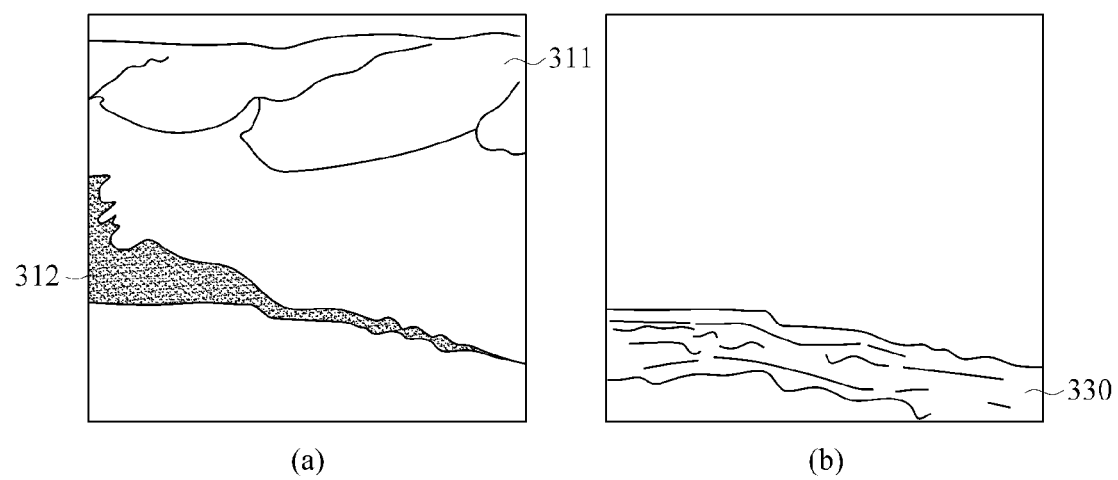

Referring to FIGS. 1 and 5B (a), the lesion detecting apparatus 100 may extract the fat tissue region 310 including the subcutaneous fat tissue region 311 and the retromammary fat region 312 from the image of the breast.

Referring to FIGS. 1 and 5B (b), the lesion detecting apparatus 100 may extract the pectoralis muscle region 330 from the image of the breast.

Figure 5C:
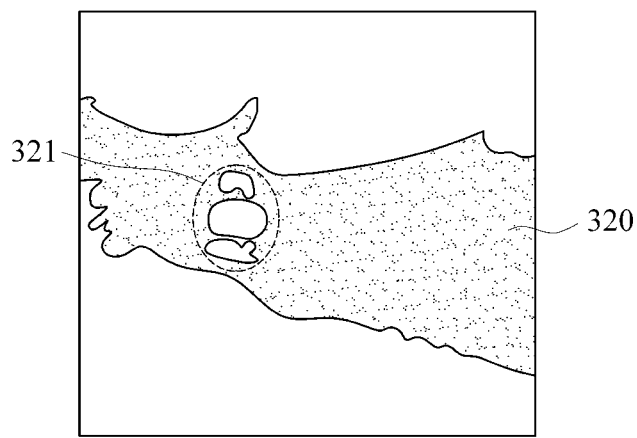

Referring to FIGS. 1 and 5C, the lesion detecting apparatus 100 may extract a region between the fat tissue region 310 and the pectoralis muscle region 330 as the mammary glandular tissue region 320. The lesion detecting apparatus 100 may set the extracted mammary glandular tissue region 320 as the lesion detection candidate region.

Figure 5D:
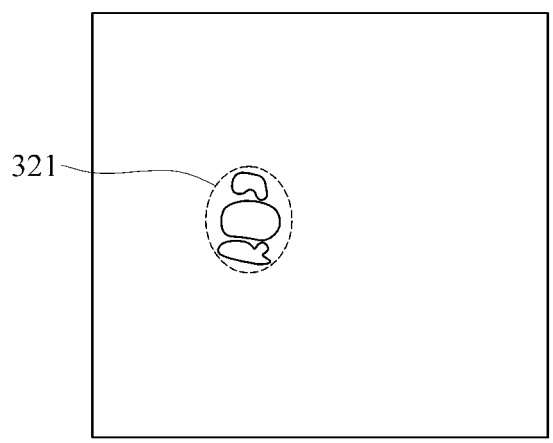

Referring to FIGS. 1 and 5D, the lesion detecting apparatus 100 may detect the lesion 321 from the lesion detecting candidate region 320. For example, the lesion detecting apparatus 100 may use of an image segmentation scheme to detect the lesion. For example, the image segmentation scheme may include a binary histogram thresholding method (BHT), a super-pixel scheme, or the like.

As described above, the lesion detecting apparatus may detect a lesion from the lesion detection candidate region having a higher chance of having lesions than other tissue regions, so there is no need for the lesion detecting apparatus to perform lesion detection on the other tissue regions having a lower chance of having lesions. Accordingly, the time used to detect lesions may be reduced and the lesions may be more precisely detected.

Figure 6:
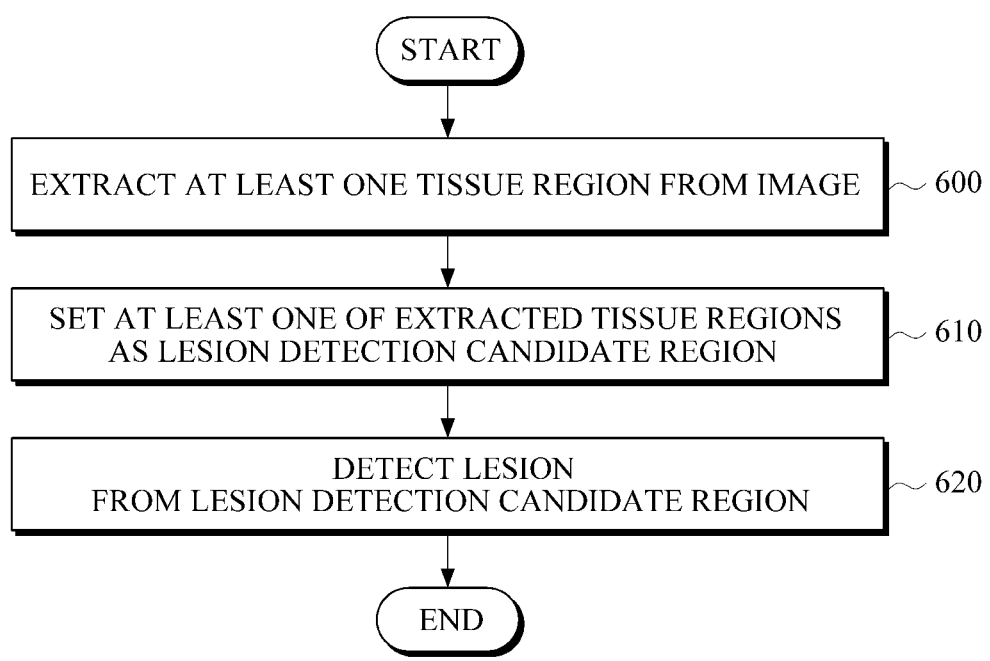
FIG. 6 is a diagram illustrating an example of a method for detecting a lesion.

FIG. 6 illustrates an example of a method for detecting a lesion.

Referring to FIG. 6, the lesion detecting apparatus extracts at least one tissue region from an image (600).

For example, the lesion detecting apparatus extracts tissue regions from an image by comparing feature information of the image with feature information of the tissue region.

The lesion detecting apparatus may partition an image into a plurality of regions by performing an image segmentation on the image, compare feature information of the partitioned region with feature information of the plurality of tissue regions, thereby extracting the tissue regions.

In response to the image being of a breast, the lesion detecting apparatus may extract at least breast tissue region from the image of the breast. For example, the lesion detecting apparatus may compare feature information of the image of the breast with feature information of the breast tissue region to extract at least one breast tissue region from the image of the breast.

For example, the lesion detecting apparatus may perform an image segmentation on the image of the breast to partition the image of the breast into a plurality of regions and compare feature information of the partitioned plurality of regions with feature information of the mammary glandular tissue region to extract the mammary glandular tissue region.

For example, the lesion detecting apparatus may detect the subcutaneous fat tissue region and the pectoralis muscle region from the image of the breasts and extract a region between the subcutaneous fat tissue region and the pectoralis muscle region as the mammary glandular tissue region.

The lesion detecting apparatus may set at least one of the extracted tissue regions as a lesion detection candidate region (610). For example, in response to the image being an image of breasts, the lesion detecting apparatus may set the mammary glandular tissue region among the breast tissue regions as the lesion detection candidate region.

The lesion detecting apparatus may detect lesions from the lesion detection candidate region (620).

According to this example of the method for detecting lesion, at least one tissue region is extracted from the image, some of the extracted tissue regions may be set as a lesion detection candidate region, and the lesion detection is performed only on the lesion detection candidate region. Accordingly, the chance of detecting a lesion is improved and the time used to detect the lesion is reduced.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for detecting a lesion, the apparatus comprising:
   a memory configured to store instructions; and
   at least one processor, that upon executing the stored instructions, is configured to:
      partition an image into a plurality of regions by performing an image segmentation,
      compare feature information of the partitioned plurality of regions to feature information of at least one tissue region,
      determine at least one region corresponding to a pre-specified type of at least one tissue region having a higher chance of having lesions than another tissue region among the partitioned plurality of regions as a lesion detection candidate region, and
      detect a lesion from the determined lesion detection candidate region,
   wherein the detection is performed on the determined lesion detection candidate region.

2. The apparatus of claim 1, wherein each of the feature information of the partitioned plurality of regions and the feature information of the at least one tissue region is represented by at least one of brightness, color, texture, relative location, and shape.

3. The apparatus of claim 1, wherein the image corresponds to an image of a breast, and the lesion detection candidate region corresponds to a mammary glandular tissue region.

4. The apparatus of claim 3, wherein the at least one processor is further configured to:
   partition the image of the breast into a plurality of regions by performing an image segmentation on the image of the breast, and compare feature information of the partitioned plurality of regions of the image of the breast with feature information of the mammary glandular tissue region to extract the mammary glandular tissue region from the image of the breast.

5. The apparatus of claim 3, wherein the at least one processor is further configured to:
partition the image of the breast into a plurality of regions by performing an image segmentation on the image of the breast, and
compare feature information of the partitioned plurality of regions with feature information of a plurality of breast tissue regions.

6. The apparatus of claim 3, wherein the at least one processor is further configured to:
extract, from the image of the breast, a subcutaneous fat tissue region and a pectoralis muscle region, and
determine, from the image of the breast, a region between the subcutaneous fat tissue region and the pectoralis muscle region as the mammary glandular tissue region.

7. The apparatus of claim 3, wherein breast tissue regions of the image of the breast comprise a subcutaneous fat tissue region, the mammary glandular tissue region, and a pectoralis muscle region.

8. The apparatus of claim 7, wherein:
feature information of the subcutaneous fat tissue region indicates an upper location of the image, a darker brightness compared to other regions, and a round shape;
feature information of the pectoralis muscle region indicates a lower location of the image and a band-like texture having a uniform direction; and
feature information of the mammary glandular tissue region indicates a location between the subcutaneous fat tissue region and the pectoralis muscle region, and a small spot-like texture.

9. The apparatus of claim 1, wherein the at least one processor is further configured to perform a morphology operation to remove noise included in the partitioned plurality of regions.

10. A method for detecting a lesion, the method comprising:
partitioning an image into a plurality of regions by performing an image segmentation;
comparing feature information of the partitioned plurality of regions to feature information of at least one tissue region;
determining at least one region corresponding to a pre-specified type of at least one tissue region having a higher chance of having lesions than another tissue region among the partitioned plurality of regions as a lesion detection candidate region; and
detecting a lesion from the determined lesion detection candidate region, the detection being performed on the determined lesion detection candidate region.

11. The method of claim 10, wherein the image is an image of a breast, and the lesion detection candidate region is a mammary glandular tissue region.

12. The method of claim 11, wherein the comparing comprises:
partitioning the image of the breast into a plurality of regions by performing an image segmentation on the image of the breast; and
comparing feature information of the partitioned plurality of regions of the image of the breast with feature information of the mammary glandular tissue region.

13. The method of claim 11, wherein the comparing comprises:
performing an image segmentation on the image of the breast to partition the image of the breast into a plurality of regions; and
comparing feature information of the partitioned plurality of regions with feature information of a plurality of breast tissue regions.

14. The method of claim 11, wherein the determining comprises:
extracting a subcutaneous fat tissue region and a pectoralis muscle region from the image of the breast; and
determining, from the image of the breast, a region between the subcutaneous fat tissue region and the pectoralis muscle region as the mammary glandular tissue region.

15. The apparatus of claim 1, further comprising:
at least one image acquisition sensor configured to photograph an inside of an organism to acquire the image,
wherein the at least one processor is further configured to determine a name of disease based on the lesion detected by the at least one processor.

16. The apparatus of claim 1, wherein the at least one processor comprises a gabor filter, a spatial gray level dependence (SGLD) filter, or a wavelet filter.

17. The apparatus of claim 1, wherein the at least one processor is further configured to utilize a window having a size of N*N or N*M to extract feature information of the partitioned plurality of regions of the image.

18. A computer program product comprising a computer readable storage medium having a computer readable program stored therein, wherein the computer readable program, when executed on a computing device, causes the computing device to:
partition an image into a plurality of regions by performing an image segmentation;
compare feature information of the partitioned plurality of regions to feature information of at least one tissue region;
determine at least one region corresponding to a pre-specified type of at least one tissue region having a higher chance of having lesions than another tissue region among the partitioned plurality of regions as a lesion detection candidate region; and
detect a lesion from the determined lesion detection candidate region,
wherein the detection is performed on the determined lesion detection candidate region.

* * * * *